US006811995B1

(12) United States Patent
Moses et al.

(10) Patent No.: US 6,811,995 B1
(45) Date of Patent: Nov. 2, 2004

(54) NON-INVASIVE ENZYME SCREEN FOR CANCER

(75) Inventors: Marsha A. Moses, Brookline, MA (US); Michael R. Freeman, Boston, MA (US); Dmitri Wiederschain, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/469,637

(22) Filed: Dec. 22, 1999

Related U.S. Application Data

(63) Continuation of application No. 08/843,095, filed on Apr. 25, 1997, now Pat. No. 6,037,138, which is a continuation-in-part of application No. 08/639,373, filed on Apr. 26, 1996, now abandoned.

(51) Int. Cl.[7] .................................................. C12Q 1/37
(52) U.S. Cl. ........................................ 435/23; 435/24
(58) Field of Search ............................ 435/23, 24, 7.92; 436/518

(56) References Cited

U.S. PATENT DOCUMENTS

| | | | |
|---|---|---|---|
| 5,270,447 A | 12/1993 | Liotta et al. | 530/326 |
| 5,324,634 A | 6/1994 | Zucker | 435/7.23 |
| 5,344,760 A | 9/1994 | Harvey et al. | 435/7.5 |
| 5,482,848 A | 1/1996 | Dickson et al. | 435/219 |
| 6,037,138 A * | 3/2000 | Moses et al. | 435/23 |
| 6,210,912 B1 | 4/2001 | Koyama et al. | 435/7.4 |
| 6,224,865 B1 * | 5/2001 | Brunner et al. | 424/130.1 |
| 6,544,761 B2 * | 4/2003 | Greene et al. | 435/69.2 |

FOREIGN PATENT DOCUMENTS

| | | |
|---|---|---|
| EP | 0 430 642 | 6/1991 |
| EP | 685 557 | 6/1995 |
| EP | 691 409 | 10/1996 |
| JP | 03 290 199 | 12/1991 |
| JP | 4-110660 | * 4/1992 |
| WO | WO 90/10228 | 9/1990 |
| WO | WO 91/11714 | 8/1991 |
| WO | WO 92/01936 | 2/1992 |
| WO | WO 93/20447 | 10/1993 |
| WO | WO 94/25434 | 11/1994 |

OTHER PUBLICATIONS

Ueda M. A Study on Cathepsin B Like Substance in Patients with Urological Cancer. Nippon Hinyokika Gakkai Zasshi 84(2)355–363, 1993.*
Aoki T. Electrophoretic Analysis of a Gastric Cancer Associated Acid Proteinase Using a Highly Sensitive Detection System. Biol Pharm Bull 17(10)1358–1363, 1994.*
Mikulewicz W. Decrease in vivo of Cysteine Endopeptidases in Blood of Patients with Tumors of the Larynx. AntiCancer Drugs 4(3)341–344, 1993.*
Guolan G. The Value of Urine Cysteine Proteinase and Serum CA125 Measurement in Monitoring the Treatment of Malignant Ovarian Tumor. Huaxi Yike Daxue Xuebao 27(3)291–294, 1996.*
Margulies I. Urinary Type IV Collagenase. Cancer Epidemiology Biomarkers and Prevention. 1(6)467–474, Sep./Oct. 1992.*
Howard E. W. Presence of MMP's in the Urine from Bladder Cancer Patients. Proc American Assoc Cancer Research vol. 35, p. 17, abstract 97, Mar. 1994.*
Davies, B. Levels of MMP's in Bladder Cancer Coreelate with Tumor Grade and Invasion. Cancer Research vol. 53, 5365–69, 1993.*
Howard, E. et al, "Presence of Matrix Metalloproteinases in Urine from Bladder Cancer Patients," Proceeding of American Association for Cancer Research Annual Meeting, vol. 35, pp. 17 (1994).
Davies, et al., "Levels of matrix Metalloproteinases in Bladder Cancer Correlate with Tumor Grade and Invasion," Cancer Research 53, pp. 5365–5369 (1993).
Attallah, A. et al.,"Comparative Study Between Cytology and Dot–ELISA for Early Detection of Bladder Cancer", A.J.C.P., vol. 102, No. 1, pp. 109–114 (1996).
Basta, M. et al., "Cytokeratin Shedding in Urine: A Biological Marker for Bladder Cancer?", British Journal of Urology, vol. 61, pp. 116–121 (1988).
Blaser, J. et al., "A Sandwich Enzyme Immunoassay for the Determination of Neutrophil Lipocalin in Body Fluids", Clinica Chimica Acta, vol. 235, pp. 137–145 (1995).
Bogdanowicz, J. et al.,"Evaluation of Prostate–Specific Antigen and Prostatic Acid Phosphatase in Untreated Prostatic Carcinoma and Benign Prostatic Hyperplasia", Scand: J. Urology Nephrol. Suppl., vol. 138, pp. 97–103 (1991).
Braunhut, S. et al., "Retinoids Modulate Endothelial Cell Production of Matrix–degrading Proteases and Tissue Inhibitors of Metalloproteinases (TIMP)", Journal of Biological Chemistry, vol. 259 (18):13472–13479 (1994).
Breul, J. et al.,"Prostate–Specific Antigen in Urine", Eur. Urol.,.vol. 26, pp 18–21 (1994).
Carr, M. et al.,"Urinary Levels of the Renal Tubular Enzyme N–Acetyl–$\beta$–D–Glucosaminidase in Unilateral Obstructive Uropathy", The Journal of Urology, vol. 151, pp. 442–445 (1994).
Fernandez–Luna, J. et al., "Measurement of Protein HC ($\alpha_1$ microglobulin) and protein HC–IgA complex in different body fluids", J. Clin. Pathol., vol. 41, pp. 1176–1179 (1988).

(List continued on next page.)

Primary Examiner—Ralph Gitomer
(74) Attorney, Agent, or Firm—Nixon Peabody LLP

(57) ABSTRACT

The present invention relates to non-invasive methods for facilitating the diagnosis of a subject as having cancer. The described methods involve detecting the presence of a matrix metalloproteinase in urine samples obtained from a patient and correlating the presence or absence of the matrix metalloproteinase with the presence or absence of cancer. Methods for monitoring the prognosis of a patient by detection of matrix metalloproteinase are also provided.

33 Claims, No Drawings

OTHER PUBLICATIONS

Fine, R., et al.,"Accumulation of Urinary Cancer–related Glycoprotein, EDCI, in Psoriasis", *Journal of Investigative Dermatology*, vol. 73, pp. 264–265 (1979).

Garnick, M. ,"Prostate Cancer: Screening, Diagnosis, and Management", *Annals of Internal Medicine*, vol. 118, pp. 804–818 (1993).

Garnick, M. , "The Dilemmas of Prostate Cancer", *Scientific American*, vol. 270 (4), pp. 72–81 (1994).

Grover, P. et al.,"Analysis of Prostatic Fluid:Evidence for the Presence of a Prospective Marker for Prostatic Cancer", *The Prostate*, vol. 26, pp. 12–18 (1995).

Ho, K. et al., "Urinary Beta–Glucuronidase Activity as an Initial Screening Test for Urinary tract Malignancy in High Risk Patients", *Cancer*, vol. 76, No. 3, pp. 473–478 (1995).

Jones, A. et al.,"Urinary N–acetyl–β–glucosaminidase Activity in Type I Diabetes Mellitus", *Ann Clin Biochem*; vol. 32, pp. 58–62 (1995).

Kossakowska, A. et al.,"Tissue Inhibitor of Metalloproteinases–1 (TIMP–1) RNA Is Expressed at Elevated Levels in Malignant Non–Hodgkin's Lymphomas", *Blood*, vol. 77 (11), pp. 2475–2481 (1991).

Lee, M. et al.,"Analysis of Affinity and Structural Selectivity in the Binding of Proteins to Glycosaminoglycans: Development of a Sensitive Electrophoretic Approach",*Biochemistry*, vol. 88, pp. 2768–2772 (1991).

Liotta, L. et al.,"Cancer Metastasis and Angiogenesis: An Imbalance of Positive and Negative Regulation", *Cell*, vol. 64, pp. 327–336 (1991).

Lu, X. et al.,"Immunological Quantitation of Levels of Tissue Inhibitor of Metalloprteinase–1 in Human Colon Cancer", *Cancer Research*, vol. 51, pp. 6231–6235 (1991).

Margulies, I. et al. "Urinary Type IV Collagenase: Elevated Levels Are Associated with Bladder Transitional Cell Carcinoma" *Cancer Epidemiology, Biomarkers & Prevention*, vol. 1, pp. 467–474 (1992).

Miller, D. et al., "Purification and Characterization of Active Human Interleukin 1β–converting Enzyme from THP.1 Monocytic Cells",*Journal of Biological Chemistry*, vol. 268 (24), pp. 18062–18069 (1993).

Moses, M. et al., "Production of Matrix Metallorproteinases and a Metalloproteinase Inhibitor by Swarm Rat Chondrosarcoma", *Biochemical and Biophysical Research Communications*, vol. 199 (1), pp. 418–424 (1994).

Paigen, B. et al., "Urinary Glucuronidase and Arylsulfatases in Identical Twins of Bladder Cancer Patients", *Cancer Research*, vol. 44, pp. 3624–3626 (1984).

Robins, S..et al.,"Direct, Enzyme–Linked Immunoassay for Urinary Deoxypyridinoline as a Specific Marker for Measuring Bone Resorption", *Journal of Bone and Mineral Research*, vol. 9, No. 10, pp. 1643–1649 (1994).

Schmitt, M. et al.,"Tumor–Associated Urokinase–Type Plasminogen Activator: Biological and Clinical Significance", *Biol. Chem.*, vol. 373, pp. 611–622 (1992).

Tetzner, E. et al.,"Osterreichische Zeitschrift fur Erforschung and Bekampfung der Krebskrankheit", *Osterr. Zschr. Krebsforsch.*, pp. 233–237 (1971) –(English Abstract Included).

Tomita, Y. et al. "Immunohistochemical Detection of Intercellular Adhesion Molecule–1 (ICAM–1) and Major Histocompatibility Complex Class I Antigens in Seminoma", *Journal of Urology*, vol. 149, pp. 659–663 (1993).

Woessner, J., "The Family of Matrix Metalloproteinases" *Annals New York Academy of Sciences*, vol. 732, 11–21 (1994).

Bianco, F.J. et al. "Matrix metalloproteinase–9 expression in bladder washes from bladder cancer patients predicts pathological stage and grade." *Clinical Cancer Research* 4(10):3011–6 (Dec. 1998).

Durkan, G.C. et al. "Prognostic significance of matrix metalloproteinase –1 and tissue inhibitor of metalloproteinase–1 in voided urine samples from patients with transitional cell carcinoma of the bladder." *Clinical Cancer Research* 7(11):3450–6 (Nov. 2001).

Kanno, N. et al. "Effects of epidermal growth factor on the invasion activity of the bladder cancer cell line." *Journal of Urology* 159(2):586–90 (Feb. 1998).

Koshida, K. et al. "Prospects for molecular research in urological oncology: bladder cancer." *Acta Urologica Japonica* 47(11):815–8 (Nov. 2001) [Japanese with English abstract].

Levitt, N.C. et al. "Phase I and pharmacological study of the oral matrix metalloproteinase inhibitor, MMI270 (CGS27023A), in patients with advanced solid cancer." *Clinical Cancer Research* 7(7):1912–22 (Jul. 2001).

Mizushima, Y. et al. "Diuretic response to cyclophosphamide in rats bearing a matrix metalloproteinase –9–producing tumour." *British Journal of Cancer* 78(8):1030–4 (Feb. 1998).

Özdemir, E. et al. "Role of matrix metalloproteinase–9 in the basement membrane destruction of superficial urothelial carcinomas." *Journal of Urology* 161(4):1359–63 (Apr. 99).

Pattari, S.K. et al. "Urine: beyond cytology for detection of malignancy." *Diagnostic Cytopathology* 27(3):139–42 (Sep. 2002).

Yan, L. et al. "The high molecular weight urinary matrix metalloproteinase (MMP) activity is a complex of gelatinase B/MMP–9 and neutrophil gelatinase–associated lipocalin (NGAL). Modulation of MMP–9 activity by NGAL." *Journal of Biological Chemistry* 276(40):37258–65 (Oct. 5, 2001).

\* cited by examiner

NON-INVASIVE ENZYME SCREEN FOR CANCER

RELATED APPLICATIONS

This application is a continuation of application Ser. No. 08/843,095, filed Apr. 25, 1997, now U.S. Pat. No. 6,037,138, which is a continuation-in-part of application Ser. No. 08/639,373 filed Apr. 26, 1996 now abandonded.

BACKGROUND OF THE INVENTION

A class of disorders may be characterized as tissue remodelling-associated conditions, and includes cancers, arthritic conditions, obstructive disorders, degenerative disorders, and problematic wound-healing and ulcerative disorders. Paradigmatic among these is prostate cancer (CaP), the leading source of new cases of cancer in men in this country, and the second leading cancer cause of cancer death after lung cancer. Over 40,000 Americans are estimated to have died of CaP in 1995, and about 244,000 new cases of prostate cancer were detected (Cancer Facts and Figures —1995, *American Cancer Society, Inc.,* 1995) and these numbers have increased annually at an alarming rate. Further, the rate of appearance of prostate cancer in African-American men is 37% higher than for their white counterparts (Jaroff, L. (Apr. 1, 1996), Time).

The current primary diagnostic tool for disorders of the prostate is measurement of the level of prostate-specific antigen (PSA) in blood, which in normal men ranges from 0 to 4 nanograms/milliliters. Prostate enlargement, a condition known as benign prostatic hyperplasia (BPH), is found in about half of men over age 45. With BPH, PSA levels rise in proportion to prostate size, possibly obscuring diagnosis of CaP. In addition, a significant proportion of men with CaP have normal PSA levels. The PSA test is somewhat non-specific for distinguishing CaP and BPH, and produces a degree of false negative results (Garnick, M., (1993), *Am. Inst. Med.,* 118:804–818). Further, the PSA test is somewhat invasive, requiring the subject to give a blood sample, a procedure that requires trained personnel, in the setting of a doctor's office or clinic. The PSA test, a major advance over previous procedures, thus leaves much to be desired.

CaP is treated by surgery, radiation therapy, cryotherapy or implantation of radioactive seeds, or a combination of these procedures. In choosing one of these treatments, consideration is also taken of possible sequelae that impact negatively on quality of life, such as temporary or long-term incontinence and impotence. Further, following surgical or chemotherapeutic treatment, production of testosterone is suppressed hormonally, to discourage metastases in the CaP patient. Hormonal suppression is found to be effective for several years duration, however cancer cells that have metastasized eventually become resistant to the drugs of hormonal suppression. CaP metastasis to other sites is inevitably fatal. Only a small percent of men with microscopically-detectable CaP progress to metastatic cancer and actually die of this disease. A current medical approach, particularly for the elderly, is "watchful waiting", wherein tumors are not treated but rather monitored for progression.

SUMMARY OF THE INVENTION

The present invention provides biological markers to non-invasively monitor the diagnosis and prognosis of prostate disorders and other tissue remodelling-associated conditions. This invention provides methods and kits using non-invasive procedures for detection of tissue remodelling-associated conditions in subjects and patients, for diagnosis of diseases such as prostate cancer, breast cancer, ovarian cancer, brain tumors, arthritic conditions, obstructive conditions, and ulcerative conditions. The primary screens use biological fluid samples that may be obtained by personnel without medical training, and do not require visiting a clinic or hospital. The statistical association between positive results and occurrence of tissue remodelling-associated conditions are applied to early diagnoses of the appearance of these conditions, and to prognoses of changes in these conditions.

The present invention features non-invasive methods for facilitating diagnosis of a subject for a tissue remodelling-associated condition. The method involves obtaining a biological sample from that subject and detecting an enzyme in that sample, facilitating the diagnosis. The non-invasive method was based at least in part, on the observation of full length, active intact enzymes that are normally associated with the process of tissue remodelling, in urine samples from patients with certain conditions. For example, gelatin-degrading matrix metalloproteinases and other proteases have been found in the urine of cancer patients. Further, high statistical associations between presence of prostate cancer and appearance of certain enzymes in urine, and between metastatic cancer and certain enzymes in urine, have been found.

The tissue remodelling conditions that can be monitored by the methods of this invention include a variety of types of cancer, moreover, the enzymes are suitable for diagnosis of other tissue remodelling conditions, such as arthritis, degenerative conditions, and obstructive conditions. The invention provides non-invasive methods for diagnosing these conditions by assay for enzymes in biological fluids.

More preferably, the methods of this invention embody detection of enzymes in urine, for diagnosis and prognosis of cancer, and most preferably, prostate cancer. The invention also relates to diagnosis and prognosis of metastatic prostate cancer. The varieties of cancer suitable for diagnosis by the methods of this invention include, among others, cancers of epithelial origin, for example, cancers of the nervous system, breast, retina, lung, skin, kidney, liver, pancreas, genito-urinary tract, ovarian, uterine and vaginal cancers, and gastrointestinal tract cancers, which form in cells of epithelial origin. Using the methods described here, cancers of mesodermal and endodermal origin, for example, cancers arising in bone or in hematopoietic cells, are also diagnosed.

In a preferred embodiment, the enzymes that are detected are matrix-digesting enzymes, more preferably, enzymes that are proteinases, and most preferably, enzymes that are metalloproteinases. In a different aspect, the methods of this invention involve enzymes that are full-length active enzymes, and they are matrix metalloproteinases. In another aspect, the method involves removal of low molecular weight contaminants from urine prior to the detection step; preferably, the urine is dialyzed to remove low molecular contaminants prior to the detection step.

Another aspect of the methods features a fully non-invasive means for facilitating the diagnosis of a subject for a disorder of the prostate. A urine sample is obtained from the subject, and a prostate disorder-associated enzyme is detected in the urine sample, facilitating the diagnosis of that subject for the prostate disorder. More preferably, the prostate disorder-associated enzyme is a matrix-digesting enzyme, most preferably, a proteinase which is a metalloproteinase. The disorders of the prostate include benign prostatic hyperplasia, "problematic" prostatic hyperplasia, organ-defined prostate cancer, this cancer which may previously have been treated surgically or chemically, and particularly, situations in which metastatic cancer is suspected. The method encompasses diagnosis of subjects who are being treated hormonally with agents that block testosterone.

The invention facilitates diagnosis of subjects for prostate cancer, using a urine sample from such subjects, and detecting one or more prostate cancer-associated enzymes. Enzymes of the matrix metalloproteinase class are among those that are diagnostic, and in the case of prostate cancer, the method involves detection of gelatinase A, gelatinase B, and related activities. More preferably, the detected metalloproteinase enzyme has a molecular weight approximately equal to 72 kDa, 92 kDa, or equal to or greater than approximately 150 kDa. Yet another feature of the invention is a method for prognosis of metastatic prostate cancer, by obtaining a biological sample from a subject and detecting a metastatic prostate cancer-associated enzyme in that biological sample facilitating the prognosis of metastatic prostate cancer. In the preferred embodiment for detecting these enzymes, low molecular weight contaminants are removed from the urine prior to the detection step.

Detection of enzymes in biological fluids may be by electrophoresis, and a preferred method of analysis of the electrophoretogram is to develop a pattern of enzyme migration mobilities as a zymogram. The zymogram involves incorporating an enzymatic substrate into the inert matrix in which the enzyme species migrate. Examples of suitable substrates are type IV collagen or a derivative of a type IV collagen, and in the Examples used here, the substrate is the collagen derivative gelatin. Other convenient protein substrates, e.g., casein, are also encompassed by the methods of the invention. Other methods of enzyme detection may be immunochemical, for example, the enzymes may be detected by radioimmune assay or by enzyme-linked immunosorbent assay.

The invention features kits for facilitating diagnosis and prognosis of tissue remodelling-associated conditions, which have a container with a reagent for detecting an enzyme in a urine sample, and instructions. In a preferred embodiment of the kit, the tissue remodelling-associated conditions being detected are one or more types of cancer, for example, organ-confined prostatic cancer, metastatic cancer, and prognosis of metastasis in a prostate cancer patient. In a different embodiment, the tissue remodelling-associated condition is an arthritic, obstructive, or degenerative condition.

DETAILED DESCRIPTION OF THE INVENTION

The present invention provides non-invasive methods, between presence of enzymes in biological fluids, and diagnosis and prognosis of tissue remodelling-associated conditions (TRACs), especially cancers, obstructive and degenerative conditions, and arthritic conditions, and kits for use for such diagnosis and prognosis. Diagnoses and prognoses for TRACs have been developed based on observed statistical associations between these conditions and the presence of a pattern of enzymes in biological fluids. For convenience, certain terms employed in the specification, examples and appended claims are collected here.

The term "subject," as used herein, refers to a living animal or human in need of diagnosis or prognosis for, or susceptible to, a condition, in particular an "tissue remodelling-associated condition" as defined below. The subject is an organism capable of responding to tissue remodelling signals such as growth factors, under some circumstances, the subject is susceptible to cancer and to arthritis. In preferred embodiments, the subject is a mammal, including humans and non-human mammals such as dogs, cats, pigs, cows, sheep, goats, horses, rats, and mice. In the most preferred embodiment, the subject is a human. The term "subject" does not preclude individuals that are entirely normal with respect to tissue remodelling-associated conditions or normal in all respects. The subject may formerly have been treated surgically or by chemotherapy, and may be under treatment by hormone therapy or have been treated by hormone therapy in the past.

The term "patient," as used herein, refers to a human subject who has presented at a clinical setting with a particular symptom or symptoms suggesting one or more diagnoses. A patient may be in need of further categorization by clinical procedures well-known to medical practitioners of the art (or may have no further disease indications and appear to be in any or all respects normal). A patient's diagnosis may alter during the course of disease progression, such as development of further disease symptoms, or remission of the disease, either spontaneously or during the course of a therapeutic regimen or treatment. In the invention here, a patient described in the Examples is listed with other patients according to the most recent diagnosis of the medical condition, and any previous diagnoses, if different, are described in the text. Thus, the term "diagnosis" does not preclude different earlier or later diagnoses for any particular patient or subject. The term "prognosis" refers to assessment for a subject or patient of a probability of developing a condition associated with or otherwise indicated by presence of one or more enzymes in a biological sample, preferably in urine.

The term "biological sample" includes biological samples obtained from a subject. Examples of such samples include urine, blood taken from a prick of the finger or other source such as intravenous, blood fractions such as serum and plasma, feces and fecal material and extracts, saliva, cerebrospinal fluid, amniotic fluid, mucus, and cell and tissue material such as cheek smear, Pap smear, fine needle aspiration, sternum puncture, and any other biopsied material taken during standard medical and open surgical procedures.

The term "invasiveness" as used here with respect to metastatic cancer (Darnell, J. (1990), *Molecular Cell Biology*, Third Ed, W.H.Freeman, NY) is distinct from the use of the term "invasive" to describe a medical procedure, and the distinction is made in context. "Invasive" for a medical procedure pertains to the extent to which a particular procedure interrupts the integrity of the body. "Invasiveness" ranges from fully non-invasive, such as collection of urine or saliva; to mildly invasive, for example a Pap smear, a cheek scrape or blood test, which requires trained personnel in a clinical setting; to more invasive, such as a sternum marrow collection or spinal tap; to extensively invasive, such as open surgery to detect the size and nature of tumors by biopsy of material, taken for example during brain surgery, lung surgery, or transurethral resection in the case of prostate cancer.

The term "invasive" is also used with respect to proclivity of a tumor for expanding beyond its boundaries into adjacent tissue, or to the characteristic of the tumor with respect to metastasis (Darnell, J. (1990), *Molecular Cell Biology*, Third Ed., W.H.Freeman, NY). For example, a basal cell carcinoma of the skin is a non-invasive or minimally invasive tumor, confined to the site of the primary tumor and expanding in size, but not metastasizing. In contrast, the cancer melanoma is highly invasive of adjacent and distal tissues. The invasive property of a tumor is often accompanied by the elaboration of proteolytic enzymes, such as collagenases, that degrade matrix material and basement membrane material to enable the tumor to expand beyond the confines of the capsule, and beyond confines of the particular tissue in which that tumor is located. Elaboration of such enzymes may be by endogenous synthesis within the tumor cells, or may be elicited from adjacent cells or by circulating neutrophils, in which cases the elicitation by the tumor results from chemical messengers elaborated by the tumor and expression of the enzymes occurs at the tumor site or proximal to the tumor. The enzymes of the present invention are not intended to be limited to those produced exclusively as endogenous tumor products, but are found in biological samples in patients in need of or subjects in need of prognosis or diagnosis of TRACs.

Cancer or neoplasia is characterized by deregulated cell growth and division. A tumor arising in a tissue originating from endoderm or exoderm is called a carcinoma, and one arising in tissue originating from mesoderm is known as a sarcoma (Darnell, J. (1990), *Molecular Cell Biology, Third Ed.*, W.H.Freeman, NY). A current model of the mechanism for the origin of a tumor is by mutation in a gene known as an oncogene, or by inactivation of a second tumor-suppressing genes (Weinberg, R. A., (September 1988), *Scientific Amer.,*44–51). The oncogenes identified thus far have arisen only in somatic cells, and thus have been incapable of transmitting their effects to the germ line of the host animal. In contrast, mutations in tumor-suppressing genes can be identified in germ line cells, and are thus transmissible to an animal's progeny. Examples of cancers include cancers of the nervous system, breast, retina, lung, skin, kidney, liver, pancreas, genito-urinary tract, gastrointestinal tract, cancers of bone, and cancers of hematopoietic origin such as leukemias and lymphomas. In one embodiment of the present invention, the cancer is not a cancer of the bladder.

An athritic condition such as rheumatoid arthritis is an example of a TRAC since the disease when chronic is,characterized by disruption of collagenous structures (J. Orten et al., (1982), *Human Biochemistry, Tenth Ed.*, C.V. Mosby, St. Louis, Mo.). Excess collagenase is produced by cells of the proliferating synovium. Other TRAC conditions such as ulcerative, obstructive and degenerative diseases are similarly characterized by alterations in the enzymes of metabolism of structural proteins.

The term "prostate cancer" (CaP) as used herein refers to both the appearance of a palpable tumor of the prostate, and also to microscopically detectable neoplastic or transformed cells in the prostate gland. In the latter case, the said cytologically-detectable prostate cancer may be asymptomatic, in that neither the patient nor the medical practitioner detects the presence of the cancer cells. It is estimated that 10 million American men carry microscopic CaP (M. Garnick, (April 1994), *Sci. Am,* 78). Cancer cells are generally found in the prostates of men who live into their seventies or eighties, however not all of these men develop prostate cancer (CaP). Autopsies show microscopic clusters of prostate cancer cells in one-third of men who die of other causes (Thayer, W., (Mar. 19, 1996), quoted in *Nutr. Act. Newsletter,* 23(2):12). Death rates from prostate cancer rise after age 55, and new cases of prostate cancer, are increasing even faster than the death rate. CaP is the second leading cause of cancer death in men, causing over 40,000 deaths in 1995. In the event that prostate cancer metastasizes to additional sites distal to the prostate, the condition is described as metastatic cancer (MC), or prostate cancer, metastasized, to distinguish this condition from organ-confined prostate cancer. CaP fatality results from metastatic dissemination of prostatic adenocarcinoma cells to distant sites, usually in the axial skeleton.

The term "organ-confined", as used herein, refers to prostate cancer that has not metastasized beyond the boundaries of the prostate gland, i.e., has not been found by techniques familiar to those skilled in the art to occur in any organs or tissues beyond the prostate gland. It can not be ruled out, however, that some number of cells have metastasized, however they are not detected by ordinary techniques used by those with skill in the art.

The term "metastasis" as used herein refers to the condition of spread of cancer from the organ of origin to additional distal sites in the patient. Preferential target organs are common to cancer types, e.g., CaP frequently metastasizes to bone, with concomitant symptoms such as back pain and acute urinary retention, and high levels of mortality. Metastatic cancer (MC) as exemplified for the purposes of this invention, is not limited to spread of CaP to bone or any particular organ, and includes also spread of other cancers such as kidneys (renal), breast, and gastrointestinal tract to organs beyond these primary sites.

The phrase "benign prostatic hypertrophy," as used herein, comprises an age-related non-cancerous enlargement of the prostate, and affects more than 50% of men over age 45 (Garnick, supra). Benign prostatic hytertrophy (BPH) may be asymptomatic, that is, have no negative consequences for the individual, and is not intended here to imply the necessary development of prostate cancer. BPH is accompanied by an increase in production of the protein prostate specific antigen (PSA discussed infra), proportional to the extent of growth of the prostate gland. For this reason, the diagnosis of CaP in a BPH patient may be difficult to distinguish from further asymptomatic growth by sole use of the PSA test (vide infra).

BPH may appear as or may progress to "problematic" prostatic hyperplasia, with symptoms that include urinary urgency, frequency, and hesitancy, and penile erectile difficulties. Since these same symptoms are associated with CaP (M. Garnick, (1993), *Annals Int. Med.,* 118(10)804–818), the clinician distinguishes CaP and problematic prostatic hyperplasia by the suddenness in onset of symptoms, and by additional diagnostic tests (described below). BPH an d problematic prostatic hypertrophy may also progress to CaP, however these terms are meant neither to exclude nor to imply disease progression, as the full range of diagnostic possibilities is found for the BPH patient population as for the normal subject.

At present, the primary diagnostic tool for prostate disorders is a blood test that measures prostate specific antigen (PSA) levels. Elevated PSA is associated both with CaP and with BPH, and PSA levels also increase with age. In cases of CaP, removal of the prostate should produce a PSA reading of zero, and a subsequent positive PSA reading in the blood indicates that the cancer has metastasized, a condition that is incurable and fatal. Cap that remains organ-confined is treated primarily by surgery and hormone therapy to block testosterone, treatments that frequently cause a variable period of incontinence and loss of libido, and may only temporarily block tumor growth or metastasis.

Hormone suppression of recurrence and metastasis of prostate cancer is possible because CaP is a sex hormone dependent cancer (Smith, P. (1995), *Cancer Surveys Vol.23: Preventing Prostate Cancer*, Imper. Cancer Research Fund); that is, the growth of the cancer is promoted by male hormones (e.g., androgens such as testosterone and dihydrotestosterone). Removal of the testes (castration) was for many years the standard method of preventing secretion of male hormones by the gonads, to reduce growth of the cancer. Currently, secretion of male hormones is suppressed by chemical means by interfering with production of luteinizing hormone (LH), which regulates synthesis of male hormones. Similar considerations are applicable to other sex hormone-dependent cancers, such as breast or ovarian cancer.

Beyond detection of elevated PSA level, other current diagnostic methods for CaP are known to medical practitioners skilled in the art and include rectal examination, transrectal ultrasonography or magnetic resonance imaging (MRI), bone scanning, X-rays, skeletal survey, intravenous pyelography, CAT-scan, and biopsy (reviewed in Garnick, M. (1993), *Annals of Internal Medicine*, 118:803–818; and Garnick, M. (1994), *Scientific American*, 270:72–81). These procedures are invasive, complex, costly, and require highly trained personnel.

CaP stages are commonly evaluated according to a scale divided as A, B, C and D. Tumors in stage A are microscopic; stage $A_1$ designates tumors confined to a relatively small area and composed of well-differentiated tissue; stage $A_2$ tumors are more diffuse and less well differentiated; stage B tumors are large enough to be felt during a rectal examination; and stage C prostate cancers have spread throughout the gland and typically have pushed past the borders of the prostate into surrounding structures. Stage D tumors have metastasized, e.g., to lymph nodes, bone, or other organs. Alternatively, tumors are also staged by the TNM staging system, in which tumors are ranked on a scale of progressively worsening disease from T1a to T4b (e.g., T1c tumors are non-palpable and non-visible that were detected by elevated blood levels of prostate specific antigen). Of tumors characterized as being is stages A2, B, or C, 25% to 50% turn out, on further testing, to be metastatic (Garnick, supra). Methods involving procedures for removal or destruction of prostatic tumor tissue usually are employed with non-metastasized cancers. For example, radical prostatectomy preferably is used with stage A, B and some stage C tumors (i.e., where the tumor growth has not extended considerably beyond the borders of the prostate gland) as well as stage T1c tumors. X-ray therapy (e.g., external or interstitial) preferably is used with stage A, B or C tumors as well as T1c tumors. Additional diagnostic tools might aid in distinguishing cases suitable for various treatments.

In the present invention, detection of a pattern of enzymes in a biological sample from a subject is used to facilitate diagnosis and prognosis of TRAC by offering statistical associations with particular conditions. The term "enzymes" is art recognized and includes protein catalysts of chemical reactions. The enzyme for purposes of this invention can be a whole intact enzyme or portions or fragments thereof. The preferred embodiment of the term enzymes as used herein, are naturally occurring enzymes that catalytically degrade proteins, i.e. the enzymes known as proteases or proteinases. By proteinase is meant a progressive exopeptidase that digest proteins by removing amino acid residues from either the N terminal or C terminal which reaction proceeds to achieve significant degradation, or an endopeptidase which destroys the amide bond between amino acid residues with varying degrees of residue specificity. The term "protease" may also include the highly specific amino acid peptidases that remove a single amino acid from an N terminus or C terminus of a protein. Examples are alanine aminopeptidase (EC 3.4.11.2) and leucine aminopeptidase (EC 3.4.11.1), which remove alanine or leucine, respectively, from the amino terminus of a protein that may have alanine and leucine, respectfully, at the amino terminus. Molecular weights of enzymes of the invention are included in, but not limited to, molecular weights in the range of approximately 20 kDa to approximately 200 kDa, more preferably 50 kDa to approximately 150 kDa.

The more preferred embodiment of the term protease designates an enzyme which can actually cause digestion of a protein yielding a product with a significantly lower molecular weight than the substrate material. The term "enzyme" includes polymorphic variants that are silent mutations naturally found within the human population. The enzymes in the best embodiment of the invention are proteases or proteinases, however there is no intent to limit the invention to these enzymes. The term proteases (and its equivalent term proteinases) is intended to include those endopeptidases and progressive exopeptidases that are capable of substantially reducing the molecular weight of the substrate and destroying its biological function, especially if that biological function of the substrate is to be a structural component of a matrix barrier. Amino acid peptidases such as alanine aminopeptidase and leucine aminopeptidase are also broadly included among proteases, however do not share the property of significantly reducing the molecular weight of the substrate protein.

Many thousands of proteases occur naturally, and each may appear at different times of development and in different locations in an organism. The invention herein features enzymes of the class of the matrix metalloproteinases (MMPs, class EC 3.4.24). These enzymes, which require a divalent cation for activity, are normally expressed early in the development of the embryo, for example, during hatching of an zygote from the zona pellucida, and again during the process of attachment of the developing embryo to the inside of the uterine wall. Enzyme activities such as N-acetylglucosaminidase (EC 3.2.1.50) appear in urine in the case of renal tubular damage, for example, due to diabetes (Carr, M., (1994), *J. Urol.* 151(2):442–445; Jones, A., et. al., (1995), *Annals. Clin. Biochem.*, 32:68–62). That these activities appear in urine as a result of renal tubular damage is irrelevant to the present invention as described herein.

The language "matrix-digesting enzyme" refers to an enzyme capable of digesting or degrading a matrix, e.g., a mixture of proteins and proteoglycans that comprise a layer in a tissue on which certain types of cells are found. Matrix-digesting enzymes are expressed during stages of normal embryogenesis, pregnancy and other processes involving tissue remodelling. In addition, some of these enzymes, for example some matrix metalloproteinases (MMPs), degrade the large extracellular matrix proteins of the parenchymal and vascular basement membranes that serve as mechanical barriers to tumor cell migration. These MMPs are produced in certain cancers and are associated with metastasis (Liotta, L. A., et al., (1991), *Cell*, 64:327–336). Examples of MMPs are the type IV collagenases, e.g., mmp-2 (gelatinase A. EC 3.4.24.24) and mmp-9 (gelatinase B, 3.4.24.35), and stromelysins (EC 3.4.24.17 and 3.4.24.22). Some MMPs are specifically inhibited by molecules called tissue inhibitors of metalloproteinases (TIMPs, Woessner, J. F., Jr., (1995), *Ann. New York Acad. Sci.*, 732:11–21), which also may be overproduced by tumor cells, however under certain conditions enzyme activity is in molar excess over the TIMPs (Freeman, M. R. et al., (1993), *J. Urol.,* 149:659; Lu, X. et al; (1991), *Cancer Res.,* 51:6231–6235,; Kossakowska, A. E. et al., (1991), *Blood,* 77:2475–2481). In one embodiment of this invention, the inhibitors of the enzyme (TIMPS, e.g., TIMP-1 or TIMP-2) may be the biological markets detected in the biological sample (e.g., complexed or free form) rather than the enzyme per se. The detection of the inhibitors can be accomplished using art-recognized techniques. Many of MMPs are translated as pro-enzymes, and may be found in a variety of structures, with ranges of molecular weights including smaller forms (45 kDa, 55 kDa, 62 kDa), and larger forms (72 kDa, 82 kDa, 92 kDa, and higher polymers such as 150 kDa and greater).

The language "prostate cancer-associated enzyme" or "prostate disorder-associated enzyme" is intended to include enzymes whose detection in a biological sample of a subject would facilitate diagnosis of prostate cancer or a prostate disorder. Examples include MMPs in a range of approximately 20 kDa to 200 kDa, more preferably approximately 50 kDa to approximately 150 kDa, e.g., more particularly approximately 72 kDa, 92 kDa, or 150 kDa. Presentation of these sizes do not preclude additional enzymes of larger or smaller sizes. In one embodiment of the invention, the enzyme is not an enzyme of a size of approximately 72 kDa or approximately 44 kDa. In addition to the MMPs, other types of proteases may be produced and activated in some types of cancer, for example, plasminogen may be expressed and activated by proteolytic cleavage to the protease plasmin (EC 3.4.21.7).

The term "electrophoresis" is used to indicate any separation system of molecules in an electric field, generally using an inert support system such as paper, starch gel, or preferably, polyacrylamide. The electrophoresis methods with polyacrylamide gels and the sodium dodecyl sulfate denaturing detergent are described in the Examples below. The protocols are not intended to exclude equivalent procedures known to the skilled artisan. Other SDS polyacrylamide procedures, known to the skilled artisan, may be used, e.g., a single polyacrylamide concentration such as 10%, may be substituted for the gradient in the separation gel. The physical support for the electrophoretic matrix may be capillary tubes rather than glass plates. Details of several SDS-polyacrylamide gel electrophoresis systems are described in many review articles and biotechnology manuals (e.g., Maniatis, T., *Molecular Cloning: A Laboratory Manual,* 2nd Edition, Cold Spring Harbor Press, Cold Spring Harbor, N.Y.). The method is not limited to use of SDS and other detergents. Further, electrophoresis in the absence of detergents may be employed. Proteins may be separated under non-denaturing conditions, for example in the presence of urea on a polyacrylamide matrix (Maniatis, supra), or by charge, for example by the procedure of isoelectric focussing.

In using an electrophoretic technique for separation of enzymes, the electrophoretogram may be developed as a zymogram. The term "zymography" is meant here to include any separations system utilizing a chemically inert separating or support matrix, that allows detection of an enzyme following electrophoresis, by exposing the matrix of the separations system to conditions that allow enzyme activity and subsequent detection. More narrowly, the term zymography designates incorporation of an appropriate substrate for the enzyme of interest into the inert matrix, such that exposing the matrix to the conditions of activity after the electrophoresis stop yields a system to visualize the precise location, and hence the mobility, of the active enzyme. By techniques well-known to the skilled artisan, the molecular weights of proteins are calculated based on mobilities derived from positions on a zymogram. Such techniques include comparison with molecular weight standards, the mobilities of which are determined from general protein stains or from pre-stains specific to those standards, and comparison with positive controls of purified isolated enzymes of interest, which are visualized by the technique of the zymogram, i.e., enzyme activity.

In particular, substrates for detection of proteases by zymography are included in the electrophoresis matrix. For type IV collagenases, the natural substrate is a type IV collagen and gelatin, a type I collagen derivative, is used for the zymography substrate in the Examples presented herein. However other proteins that are suitable for detection of further proteases of interest in TRAC diagnosis, for example, include fibronectin; vitronectin; collagens of types I through III and V through XII; procollagens; elastin; laminin; plasmin; plasminogen; entactin; nidogen; syndecan; tenascin; and sulfated proteoglycans substituted with such saccharides as hyaluronic acid, chondroitin-6-sulfate, condroitin4-sulfate, heparan sulfate, keratan sulfate, and dermatan sulfate and heparin. Further, convenient inexpensive substrate proteins such as casein, which may not be the natural target of a protease of interest, but are technically appropriate, are included as suitable substrate components of the zymography techniques of the present invention. Chemically synthesized mimetics of naturally occurring protein substrates are also potential zymography substrates, and may even be designed to have favorable properties, such chromogenic or fluorogenic ability to produce a color or fluorescent change upon enzymatic cleavage.

Zymography may be adapted to detection of a protease inhibitor in the biological sample. Since a variety of natural MMP inhibitors are elaborated, such as TIMP-1 and TIMP-2, and are found to be deregulated during TRAC situations, the present invention includes detection of enzyme inhibitors as well as the enzymes of tissue remodelling. Thus for example, a "reporter enzyme" for which enzyme an inhibitory activity is being measured, may be incubated with each biological sample obtained by subjects and patients, in one or more quantities corresponding to one or more aliquots of sample, prior to electrophoresis. This enzyme is omitted from one aliquot of the biological sample. The inhibitory presence in the sample is detected as disappearance or decrease of the reporter enzyme band from the developed zymogram. Alternatively, functional enzyme activity assays which include in the reaction mix a known level of active enzyme, to which is added aliquots of experimental samples with putative inhibitory activity, can detect the presence of inhibitors.

Further, the enzymes of tissue remodelling extend to enzyme activities beyond those of proteolytic activity. For example, enzymes that are substituted with residues such as glycosyl, phosphate, sulfate, lipids and nucleotide residues (e.g. adenyl) are well-known to those skilled in the art. These residues are in turn added or removed by other enzymes, e.g., glycosidases, kinases, phosphatases, adenyl transferases, etc. Convenient detection methods for the presence of such activities for TRAC diagnosis and prognosis are readily developed by those with skill in the art, and are intended to comprise part of the invention here.

If activities are found in urine associated with renal damage, these may be detected by the methods described here, in which case positive data obtained with the methods of the present invention must be evaluated by including renal damage as a causative condition. Overlap between renal damage and TRAC diagnoses of course exist, e.g., renal cancer, renal tubule obstruction, renal ulcers, etc. The utility of the present invention is not construed as limited by the possibilities of an overlap, nor limited by knowledge of such conditions.

The zymogram as described in the Examples herein is developed by use of a general stain for protein, in this case, Coomassie Blue dye. The development is possible with general protein stains, e.g., Amido Black dye, and SYPRO Orange stain (Biorad Laboratories, Hercules, Calif., 94537). Further, enzyme activity may be detected by additional techniques beyond that of a clear zone of digestion in a stained matrix, for example, by absence of areas of radioactivity with a radio-labelled substrate, by change in mobility of a radio-labelled substrate, or by absence of or change in mobility of bands of fluorescence or color development with use of fluorogenic or chromogenic substrates, respectfully.

Quantitative densitometry can be performed with zymograms by placing the gel directly on an activated plate of a Molecular Dynamics phosphorimager (Molecular Dynamics, 928 East Arques Ave., Sunnyvale, Calif. 94086), or with a Datacopy G8 plate scanner attached to a MacIntosh computer equipped with an 8-bit videocard and McImage (Xerox Imaging Systems). Background measurements, areas of the gel separate from sample lanes, can similarly be scanned, and values subtracted from the readings for enzyme activities.

Another electrophoretically-based technique for analysis of a biological sample for presence of specific proteins is an affinity-based mobility alteration system (Lander, A., (1991), *Proc. Natl. Acad Sci. U.S.*, 88(7):2768–2772). An MMP or other type of enzyme of interest might be detected, for example, by inclusion of a substrate analog that binds essentially irreversibly to the enzyme, hence decreasing the mobility. The affinity material is present during electrophoresis, and is incorporated into the matrix, so that detection of the enzyme of interest occurs as a result of alteration of mobility in contrast to mobility in the absence of the material. Yet another technique of electrophoretic protein separation is based on the innate charge of a protein as a function of the pH of the buffer, so that for any protein species, there exists a pH at which that protein will not migrate in an electric field, or the isoelectric point, designated pI. Proteins of a biological sample, such as a urine sample, may be separated by isoelectric focussing, then developed by assaying for enzymatic activity for example by transfer to material with substrate, i.e., zymography. Electrophoresis is often used as the basis of immunological detections, in which the separation step is followed by physical or electrophoretic transfer of proteins to an inert support such as paper or nylon (known as a "blot"), and the blotted pattern of proteins may be detected by use of a specific primary binding (Western blot) by an antibody followed by development of bound antibodies by secondary antibodies bound to a detecting enzyme such as horse radish peroxidase. Additional immunological detection systems for TRAC enzymes are now described in detail below.

The term "antibody" as used herein is intended to include fragments thereof which are also specifically reactive with one of the components in the methods and kits of the invention. Antibodies can be fragmented using conventional techniques and the fragments screened for utility in the same manner as described above for whole antibodies. For example, $F(ab)_2$ fragments can be generated by treating an antibody with pepsin. The resulting $F(ab)_2$ fragment can be treated to reduce disulfide bridges to produce Fab fragments.

The term "antibody" is further intended to include single chain, bispecific and chimeric molecules. The term "antibody" includes possible use both of monoclonal and polyclonal antibodies (Ab) directed against a target, according to the requirements of the application.

Polyclonal antibodies can be obtained by immunizing animals, for example rabbits or goats, with a purified form of the antigen of interest, or a fragment of the antigen containing at least one antigenic site. Conditions for obtaining optisal immunization of the animal, such as use of a particular immunization schedule, and using adjuvants e.g. Freund's adjuvant, or immunogenic substituents covalently attached to the antigen, e.g. keyhole limpet hemocyanin, to enhance the yield of antibody titers in serum, are well-known to those in the art. Monoclonal antibodies are prepared by procedures well-known to the skilled artisan, involving obtaining clones of antibody-producing lymphocyte, i.e. cell lines derived from single cell line isolates, from an animal, e.g. a mouse, immunized with an antigen or antigen fragment containing a minimal number of antigenic determinants, and fusing said clone with a myeloma cell line to produce an immortalized high-yielding cell line. Many monoclonal and polyclonal antibody preparations are commercially available, and commercial service companies that offer expertise in purifying antigens, immunizing animals, maintaining and bleeding the animals, purifying sera and IgG fractions, or for selecting and fusing monoclonal antibody producing cell lines, are available.

Specific high affinity binding proteins, that can be used in place of antibodies, can be made according to methods known to those in the art. For example, proteins that bind specific DNA sequences may be engineered, (Ladner, R. C., et. al., U.S. Pat. No. 5,096,815), and proteins that bind a variety of other targets, especially protein targets (Ladner, R. C., et. al., U.S. Pat. No. 5,233,409; Ladner, R. C., et. al., U.S. Pat. No. 5,403,484) may be engineered and used in the present invention for covalent linkage to a chelator molecule, so that a complex with a radionuclide may be formed under mild conditions. Antibodies and binding proteins can be incorporated into large scale diagnostic or assay protocols that require immobilizing the compositions of the present invention onto surfaces, for example in multi-well plate assays, or on beads for column purifications.

General techniques to be used in performing various immunoassays are known to those of ordinary skill in the art. Moreover, a general description of these procedures is provided in U.S. Pat. No. 5,051,361 which is incorporated herein by reference, and by procedures known to the skilled artisan, and described in manuals of the art (Ishikawa, E., et. al. (1988), *Enzyme Immunoassay* Igaku-shoin, Tokyo, NY; Hallow, E. and D. Lane, *Antibodies: A Laboratory Manual*, CSH Press, NY). Examples if several immunoassays are given discussed here.

Radioimmunoassays (RIA) utilizing radioactively labeled ligands, for example, antigen directly labeled with $^3H$, or $^{14}C$, or $^{125}I$, measure presence of MMP's as antigenic material. A fixed quantity of labeled MMP antigen competes with unlabeled antigen from the sample for a limited number of antibody binding sites. After the bound complex of labeled antigen-antibody is separated from the unbound (free) antigen, the radioactivity in the bound fraction, or free fraction, or both, is determined in an appropriate radiation counter. The concentration of bound labeled antigen is inversely proportional to the concentration of unlabeled antigen present in the sample. The antibody to MMP can be in solution, and separation of free and bound antigen MMP can be accomplished using agents such as charcoal, or a second antibody specific for the animal species whose immunoglobulin contains the antibody to MMP. Alternatively, antibody to MMP can be attached to the surface of an insoluble material, which in this case, separation of bound and free MMP is performed by appropriate washing.

Immunoradiometric assays (IRMA) are immunoassays in which the antibody reagent is radioactively labeled. An IRMA requires the production of a multivalent MMP conjugate, by techniques such as conjugation to a protein e.g., rabbit serum albumin (RSA). The multivalent MMP conjugate must have at least 2 MMP residues per molecule and the MMP residues must be of sufficient distance apart to allow binding by at least two antibodies to the MMP. For example, in an IRMA the multivalent MMP conjugate can be attached to a solid surface such as a plastic sphere. Unlabeled "sample" MMP and antibody to MMP which is radioactively labeled are added to a test tube containing the multivalent MMP conjugate coated sphere. The MMP in the sample competes with the multivalent MMP conjugate for MMP antibody binding sites. After an appropriate incubation period, the unbound reactants are removed by washing and the amount of radioactivity on the solid phase is determined. The amount of bound radioactive antibody is inversely proportional to the concentration of MMP in the sample.

Other preferred immunoassay techniques use enzyme labels such as horseradish peroxidase, alkaline phosphatase, luciferase, urease, and β-galactosidase. For example, MMP's conjugated to horseradish peroxidase compete with free sample MMP's for a limited number of antibody combining sites present on antibodies to MMP attached to a solid surface such as a microtiter plate. The MMP antibodies may be attached to the microtiter plate directly, or indirectly, by first coating the microtiter plate with multivalent MMP conjugates (coating antigens) prepared for example by conjugating MMP with serum proteins such as rabbit serum albumin (RSA). After separation of the bound labeled MMP from the unbound labeled MMP, the enzyme activity in the bound fraction is determined calorimetrically, for example by a multi-well microtiter plate reader, at a fixed period of time after the addition of horseradish peroxidase chromogenic substrate.

Alternatively, the antibody, attached to a surface such as a microtiter plate or polystyrene bead, is incubated with an aliquot of the biological sample. MMP present in the fluid will be bound by the antibody in a manner dependent upon the concentration of MMP and the association constant between the two. After washing, the antibody/MMP complex is incubated with a second antibody specific for a different epitope on MMP distal enough from the MMP-specific antibody binding site such that steric hindrance in binding of two antibodies simultaneously to MMP may be accomplished. For example, the second antibody may be specific for a portion of the proenzyme sequence. The second antibody can be labeled in a manner suitable for detection, such as by radioisotope, a fluorescent compound or a covalently linked enzyme. The amount of labeled secondary antibody bound after washing away unbound secondary antibody is proportional to the amount of MMP present in the biological sample.

The above examples of preferred immunoassays describe the use of radioactively and enzymatically labeled tracers. Assays also may include use of fluorescent materials such as fluorescein and analogs thereof, 5-dimethylaminonaphthalene-1-sulfonyl derivatives, rhodamine and analogs thereof, coumarin analogs, and phycobiliproteins such as allophycocyanin and R-phycoerythrin; phosphorescent materials such as erythrosin and europium; luminescent materials such as luminol and luciferin; and sols such as gold and organic dyes. In one embodiment of the present invention, the biological sample is treated to remove low molecular weight contaminants.

In one embodiment of the present invention, the biological sample is treated to remove low molecular weight contaminants, for example, by dialysis. By the term "dialysis" this invention includes any technique of separating the enzymes in the sample from low molecular weight contaminants. The Examples use Spectra/Por membrane dialysis tubing with a molecular weight cut-off (MWCO) of 3,500, however other products with different MWCO levels are functionally equivalent. Other products include hollow fiber concentration systems consisting of regenerated cellulose fibers (with MWCO of 6,000 or 9,000) for larger volumes; a multiple dialyzer apparatus with a sample size for one to 5 ml; and multiple microdialyzer apparatus, convenient for samples in plates with 96 wells and MWCOs at 5,000, 8,000 and 10,000, for example. These apparatuses are available from PGC Scientific, Gaithersburg, Md., 20898. Those with skill in the art will appreciate the utility of multiple dialysis units, and especially suitable for kits for reference lab and clinic usage. Other equivalent techniques include passage through a column holding a resin or mixture of resins suitable to removal of low molecular weight materials. Resins such as BioGel (BioRad, Hercules, Calif.) and Sepharose (Pharmacia, Piscataway, N.J.) and others are well-known to the skilled artisan. The technique of dialysis, or equivalent techniques with the same function, are intended to remove low molecular weight contaminants from the biological fluids. While not an essential component of the present invention, the step of removal of such contaminants facilitates detection of the disorder-associated enzymes in the biological samples.

The invention is further illustrated by the following examples, which should not be construed as further limiting. The contents of all references, pending patent applications and published patents, cited throughout this application are hereby expressly incorporated by reference.

EXAMPLES

The following methodology described in the Materials and Methods section was used throughout these Examples, set forth below.

Material and Methods

Patient Groups

Urine samples were obtained from subjects with clinically-determined cancers of the following types: prostate cancer (13 subjects, Table 1), metastatic cancer (9 subjects, Table 2), and other non-metastatic malignancies in a variety of organs (11 subjects, Table 3). Further, urine samples were obtained from subjects with no history of cancer (13 subjects, Table 4), with benign prostatic hyperplasia. (8 subjects Table 5), with no evidence of disease (15 subjects, Table 6), and under treatment by hormonal suppression (4 subjects, Table 7). Urine samples of breast cancer patients were tested for the presence of menstrual blood using Ames Multistix 7 reagent strips (Miles, Elkhardt, Ind.), and those containing blood were not analyzed further. These specimens were analyzed by gelatin zymography, and the results were recorded as positive for each protein band with gelatinase activity observed in the lane corresponding to that urine sample.

Preparation of Samples

Urine samples were kept frozen until assay, thawed overnight at 4 C, and a 10 ml aliquot was dialyzed against double-distilled water in 45 mm dialysis tubing (Spectra/Por membrane MWCO: 3,500, Spectrum, Houston, Tex.). Following dialysis, urine samples were centrifuged at 4,000 rpm for 5 min at 4 C, the supernatant was taken and stored at 4 C prior to analysis. Analysis of urine for enzyme activity was by zymography, comprising gel electrophoresis performed in the presence of enzyme substrate followed by in situ digestion.

Electrophoresis

Polyacrylamide gel electrophoresis in the presence of sodium dodecyl sulfate (SDS) and 0.1% (w/v) gelatin was used in the Examples here. A sample comprising 30 microliters of dialyzed urine was mixed with 15 microliters of sample buffer consisting of 4% SDS, 0.15 Tris pH 6.8, 20% (v/v) glycerol, and 0.5% (w/v) bromphenol blue. Samples were applied to slots in a 4% stacking gel above a 10% polyacrylamnide separating gel on a mini-gel slab gel apparatus (Mini-Protein II, Bio-Rad).

Zymography

Following electrophoresis, gels were incubated for 30 min in 2.5% Triton X-100 (v/v) to remove SDS, rinsed, and incubated overnight at 37 C in substrate buffer (0.05 M Tris, pH 8.5, 5 mM $CaCl_2$, 0.02% sodium azide). To visualize bands of active enzyme, were stained for protein in 0.5% (w/v) Coomassie Blue R-250 in acetic acid:isopropanol:water (1:3:6), then destained in acetic acid ethanol water (1:3:6). Enzyme activity appeared as clear bands in the dark background, corresponding to the lane for each sample. The electrophoretic mobility of each clear band was determined by correlation with molecular weight protein standards and positive controls (purified mmp2 and mmp-9 proteins). The molecular weight of each band of active enzyme was recorded according to the following criteria: greater than 150 kDa, 92 kDa, 72 kDa, and other molecular weights (for example, 100 kDa and 20 kDa). The identity of these MMPs was confirmed by western blot analysis using anti-MMP antibodies (Oncogene Sciences, Cambridge, Mass.).

To verify that enzyme activities observed by zymography detected were metal-dependent proteases, samples were subjected also to incubation in substrate buffer in the presence of 1,10-phenanthroline, an MMP inhibitor.

Normal Controls

Samples of urine from 13 young healthy male subjects revealed 8 positives of 52 possible metalloproteinase bands (15%, Table 1). Thus, 4 of 13 (31%) healthy subjects had detectable gelatinase activity in urine. Analysis of the distribution of the enzyme activity shows that none of the urine samples contained enzyme activity of 72 kDa size.

TABLE 1

Zymograms of Normal Subjects (13 subjects)

| Code | >150 kDa | 92 kDa | 72 kDa | other MMPs |
|---|---|---|---|---|
| No-1 | yes | yes | no | no |
| No-2 | no | no | no | no |
| No-3 | no | no | no | no |
| No-4 | no | no | no | no |
| No-5 | no | no | no | no |
| No-6 | yes | yes | no | no |
| No-7 | no | yes | no | no |
| No-8 | yes | yes | no | yes |
| No-9 | no | no | no | no |

TABLE 1-continued

Zymograms of Normal Subjects (13 subjects)

| Code | >150 kDa | 92 kDa | 72 kDa | other MMPs |
|---|---|---|---|---|
| No-10 | no | no | no | no |
| No-11 | no | no | no | no |
| No-12 | no | no | no | no |
| No-13 | no | no | no | no |

Subjects No-1 through No-13 are normal, and have no medical history of cancer.

Example 1

Enzyme Activity in Urine of Prostate Cancer Patients and Other Cancer Patients

Analysis of urine of CaP patients showed gelatinase in 12 of the 13 samples (Table 2) Thus 92% of urine from CaP patients contained a band of 92 kDa or higher molecular weight, and 48% of the 52 possible zymogram activity categories are positive for the CaP group. These frequencies are over 3-fold higher than comparable findings for the urines from the normal controls.

Urine samples from 5 out of 11 of patients with other types of cancer showed metalloproteinase activity (Table 3). Enzymes were found in urine from 3 out of 5 bladder cancer patients, and in urine from one out of 2 patients with renal cancer, and one out of 2 patients with lymphoma.

Example 2

Enzyme Activity in Urine of Metastatic Cancer Patients

In the MC patient group, urine samples of all 8 patients displayed metalloproteinase activity (Table 4). Of the 32 possible enzyme band categories recorded, 66% were positive for patients with metastatic cancer. Further, the urine of all MC patients contained either enzyme of 92 kDa size, enzyme of molecular weight greater than 150 kDa, or both.

TABLE 2

Zymograms of Subjects with Prostate Cancer (13 subjects)

| Code | >150 kDa | 92 kDa | 72 kDa | other MMPs |
|---|---|---|---|---|
| CaP-1 | yes | yes | yes | no |
| CaP-2 | yes | yes | yes | no |
| CaP-3 | yes | yes | yes | no |
| CaP-4 | yes | yes | yes | no |
| CaP-5 | no | yes | no | no |
| CaP-6 | no | yes | no | no |
| CaP-7 | yes | yes | no | no |
| CaP-8 | no | yes | no | no |
| CaP-9 | no | no | no | no |
| CaP-10 | no | yes | no | no |
| CaP-11 | yes | yes | no | no |
| CaP-12 | yes | yes | yes | no |
| CaP-13 | yes | yes | no | no |

Subjects Cap-1 through CaP-13 are prostate cancer patients.

TABLE 3

Zymograms of Subjects with Other Cancers, Non-Metastatic (11 subjects)

enzyme pattern in urine

| Code | >150 kDa | 92 kDa | 72 kDa | other MMPs | cancer |
|---|---|---|---|---|---|
| CaB-1 | no | no | no | no | bladder |
| CaB-2 | no | no | no | no | bladder |
| CaB-3 | yes | yes | no | no | bladder |
| CaB-4 | yes | yes | yes | no | bladder |
| CaB-5 | yes | yes | no | yes | bladder |
| CaR-1 | no | no | no | no | renal |
| CaR-2 | yes | yes | yes | yes | renal |
| CaLy-1 | no | no | no | no | lymphoma |
| CaLy-2 | yes | yes | no | no | lymphoma |
| CaT-1 | no | no | no | no | testis |
| CaPh-1 | no | no | no | no | pheo-chromo-cytoma |

Five subjects with bladder cancer are indicated CaB-1 through -5. CaR-1 and -2 are subjects with renal cancer. CaLy-1 and -2 are subjects with lymphoma, CaT-1 is a testicular cancer patient, and CaPH-1 has pheochromocytoma.

TABLE 4

Zymograms of Subjects with Metastatic Cancer (8 subjects)

enzyme pattern in urine

| Code | >150 kDa | 92 kDa | 72 kDa | other MMPs |
|---|---|---|---|---|
| Meta-1 | yes | yes | yes | no |
| Meta-2 | yes | yes | yes | yes |
| Meta-3 | yes | yes | no | no |
| Meta-4 | yes | yes | no | no |
| Meta-5 | yes | yes | no | yes |
| Meta-6 | no | yes | no | no |
| Meta-7 | yes | no | no | yes |
| Meta-8 | yes | yes | yes | yes |

Subjects MC-1 through -8 are metastatic cancer patients.

TABLE 5

Zymograms of Subjects with Benign Prostatic Hyperplasia (8 subjects)

enzyme pattern in urine

| Code | >150 kDa | 92 kDa | 72 kDa | other MMPs |
|---|---|---|---|---|
| BPH-1 | yes | yes | no | no |
| BPH-2 | yes | yes | no | no |
| BPH-3 | no | yes | no | no |
| BPR-4 | no | yes | no | no |
| BPH-5 | no | yes | no | no |
| BPH-6 | no | no | no | no |
| BPH-7 | no | no | no | no |
| BPH-8 | yes | yes | no | yes |

Subjects indicated BPH-1 through -8 have benign prostatic hyperplasia.

Example 3

Enzyme Activity in Urine of Subjects with Benign Prostatic Hypertrophy

Eight subjects with BPH were assayed for metalloproteinase content of urine (Table 5). Of the 32 possible enzyme pattern observations, 10 were positive (31%), and 6 of these 8 patients (75%) had urine containing one or more bands of activity, a frequency higher than that of the normal subjects and those with no evidence of disease. None of the BPH subjects' urines (0%) showed 72 kDa metalloproteinase band. The MMP pattern of the BPH subjects as a function of time can be used to facilitate prognosis of patients likely to develop problematic BPH or other conditions.

Example 4

Enzyme Activity in Urine of Subjects with No Evidence of Disease

Fifteen subjects with previous medical histories of cancer, with no recent evidence of disease, and under regular clinical observation, were assayed for metalloproteinase content of urine. Three (20%) of the subjects' urine were found to contain enzyme (Table 6). None of these specimens contained 72 kDa metalloproteinase, and 12% (7 of 60 possible band recordings) of the possible band data from this group were positive. Most of these patients were at one time under treatment for cancer, and have exhibited no symptoms in the recent past and at the time of collection of urine samples. The frequencies of positive results were consistent with that of normal subjects.

Example 5

Enzyme Activity in Urine of Subjects under Hormonal Suppression

Table 7 shows data on metalloproteinase activity pattern in the urine specimens of 4 patients diagnosed with prostate cancer in the past, and currently under treatment by hormonal suppression. Of the 16 possible data entries, one is positive (6%), and thus one of the 4 patients has MMP activity in the urine (25%). The urine enzyme patterns of patients under hormonal suppression, which is used to prevent or delay return of prostate cancer, shows reduced frequency of positive metalloproteinase bands in urine compared to the cancer groups.

TABLE 6

Zymograms of Subjects with No Evidence of Disease (15 subjects)

enzyme pattern in urine

| Code | >150 kDa | 92 kDa | 72 kDa | other MMPs |
|---|---|---|---|---|
| NeD-1 | no | no | no | no |
| NeD-2 | no | no | no | no |
| NeD-3 | no | no | no | no |
| NeD-4 | yes | yes | no | no |
| NeD-5 | no | no | no | no |
| NeD-6 | no | no | no | no |
| NeD-7 | no | no | no | no |
| NeD-8 | no | no | no | no |
| NeD-9 | no | no | no | no |
| NeD-10 | no | no | no | no |
| NeD-11 | yes | yes | no | no |
| NeD-12 | no | no | no | no |
| NeD-13 | no | no | no | no |
| NeD-14 | yes | yes | no | yes |
| NeD-15 | no | no | no | no |

NeD-1 through -15 are subjects with prior history of cancer and with no evidence of disease in recent medical history and at the time of the urine sample.

TABLE 7

Zymograms of Hormonally Suppressed Subjects (4 subjects)

enzyme pattern in urine

| Code | >150 kDa | 92 kDa | 72 kDa | other MMPs |
|---|---|---|---|---|
| HS-1 | no | no | no | no |
| HS-2 | no | no | no | no |
| HS-3 | no | no | no | no |
| HS-4 | no | yes | no | no |

HS-1, -2, -3 and -4 are subjects with a history of prostate cancer, under treatment by hormonal suppression.

TABLE 8

Summary of Urine Metalloproteinase Activities in 4 Molecular Weight Categories for All Subjects

| diagnostic category | number positive/total | percent positive |
|---|---|---|
| normal (no cancer history) | 8/52 | 15% |
| prostate cancer, organ confined | 25/52 | 48% |
| other cancers (non-metastatic) | 14/43 | 33% |
| metastatic cancer | 21/32 | 66% |
| benign prostatic hyperplasia | 10/32 | 31% |
| no evidence of disease | 7/60 | 12% |
| hormonal suppression | 1/16 | 6% |

TABLE 9

Summary of 92 kDa Metalloproteinase in Urine

| diagnostic status | number positive/total | percent positive |
|---|---|---|
| normal (no cancer history) | 4/13 | 31% |
| prostate cancer, organ confined | 12/13 | 92% |
| other cancers (non-metastatic) | 5/11 | 46% |
| metastatic cancer | 7/8 | 88% |
| benign prostatic hyperplasia | 6/8 | 75% |
| no evidence of disease | 3/15 | 20% |
| hormonal suppression | 1/4 | 25% |

These data, for subjects in Examples 1–15 above, are summarized in Table 8 by diagnostic category of the subjects. Table 8 shows that 48% of the categories of metalloproteinase molecular species from urine of subjects with organ-confined prostate cancer, and 66% of those with metastatic cancer, were positive bands of enzyme activity. Controls of urine from normal subjects, from subjects with no evidence of disease, and from hormonally suppressed subjects with a history of prostate cancer, were 15%, 12% and 6%, respectively.

TABLE 10

Summary of 72 kDa Metalloproteinase Activity in Urine

| diagnostic status | number positive/total | percent positive |
|---|---|---|
| normal (no cancer history) | 0/13 | 0% |
| prostate cancer, organ confined | 5/13 | 38% |
| other cancers (non-metastatic) | 2/11 | 18% |
| metastatic cancer | 3/8 | 38% |
| benign prostatic hyperplasia | 0/8 | 0% |
| no evidence of disease | 0/15 | 0% |
| hormonal suppression | 0/4 | 0% |

The presence of enzyme activity of 72 kDa MMP in urine (Table 10) is uniquely found in urine from the cancer groups: 38% of subjects with organ-confined prostate cancer (5 of 13) contained this metalloproteinase, compared to none of the subjects in any of the non-cancer groups. The data show that the pattern of presence of particular of full-length metalloproteinase mmp-2 and mmp-9 proenzymes, and of high molecular weight MMPs (greater than 150 kDa), are diagnostic and prognostic tools.

Example 6
Statistical Analysis of Urine MMP Enzyme Patterns in Urine as a Cancer Marker The urinary MMP pattern data were submitted for statistical analysis using logistic regression, in which prostate and other non-metastatic cancer patients versus the combination of the normal and no evidence of disease (NeD) group is considered the binary outcome.

Comparing normal/NeD versus Cancer, the univariate results of the analysis, for greater than 150 kDa, 92 kDa and 72 kDa MMPs were that a significantly higher proportion of each of these MMP categories was detected in patients with cancer. The "other MMP" category was not significantly different between the cancer group and normal/NeD, i.e., not a significant predictor. Further, the odds are roughly 5 times higher for cancer patients to have MMP of greater than 150 kDa molecular weight detected in the urine compared to normal/NeD (the odds ratio equals 5.38, with a 95% confidence interval of 1.80 to 16.12, likelihood ratio chi-square test is 9.80, probability equals 0.002). The odds of detecting 92 kDa MMP are 7 times greater for the cancer patient group compared to normal/NeD (the odds ratio equals 7.09, with a 95% confidence interval of 4.53 to 40.67, likelihood ratio chi-square test is 13.57, probability less than 0.001). The odds of detecting 72 kDa are estimated to be infinitely higher for those patients with cancer (likelihood ratio chi-square test is 14.07, probability less than 0.001) than the normal/NeD group.

The multivariate analysis establishes the most important MMP markers and controls. The analysis indicates that 92 kDa and 72 kDa MMPs are both significant independent predictors of cancer (probability equals 0.01 for each). An estimate of the probability of cancer for combinations of two independent multivariate predictors is shown in Table 11. Subjects with urinary 72 kDa MMP or with both 92 kDa and 72 kDa MMPs have very high probabilities of having cancer, according to this analysis.

The probabilities of cancer predicted for eight possible combinations of the three univariate predictors are shown in Table 12.

Example 7
Statistical Analysis of Urine MMP Enzyme Pattern as Metastatic Cancer Markers.

Statistical methods were used to compare the urinary MMP patterns of subjects from the normal/NeD group versus patients with metastasized cancers (MC). Ninety-five percent confidence limits were derived using Pratt's method (Blyth, C. R., 1986, J.Am. Stat. Assoc. 81: 843–855). For univariate analysis, the results indicate that patients with MC are more likely to have each MMP present in urine compared to normal/NeD. Patients with MC were nearly 13 times more likely to have MMP of greater than 150 molecular weight present in urine than normal/NeD (probability equals 0.002), and 10 times more likely to have 92 kDa MMP (probability equals 0.005) and 72 kDa MMP (probability equals 0.002). A higher proportion of patients with MC compared to subjects in the normal/NeD group had other urinary MMPs (probability equals 0.014).

Using multivariate analysis, the results for MC are that the 92 kDa and 72 kDa MMPs were significant independent predictors (probability less than 0.05 for each). Modeling the estimated probabilities of MC based on the 4 variant combinations of 92 kDa and 72 kDa detected in the urine yielded the data in Table 13.

TABLE 11

Probability of Cancer Predicted from the Combination of Two Independent Multivariate Predictors, 92 kDa and 72 kDa MMP in Urine.

| 92 kDa | 72 kDa | Probability of Cancer (%) |
|---|---|---|
| − | − | 34.38 |
| + | − | 68.18 |
| − | + | 99.96 |
| + | + | 99.99 |

TABLE 12

Probability of Cancer Predicted from Urine MMP Pattern Combination of 3 Univariate Predictors.

| 150 kDa | 92 kDa | 72 kDa | Probability of Cancer (%) |
|---|---|---|---|
| − | − | − | 34.53 |
| − | − | + | 99.99 |
| − | + | − | 71.62 |
| + | − | − | 29.69 |
| − | + | + | 99.99 |
| + | + | − | 66.89 |
| + | − | + | 99.95 |
| + | + | + | 99.99 |

TABLE 13

Probability of Metastatic Cancer Predicted from Urine MMP Pattern of Two Univariate Predictors.

| 92 kDa | 72 kDa | Probability of MC (%) |
|---|---|---|
| − | − | 8.69 |
| + | − | 36.36 |
| − | + | 99.94 |
| + | + | 99.99 |

TABLE 15

Statistical Performance Characteristics for Urine MMP Markers*

| marker | sensitivity (95% CI) | specificity (95% CI) | positive LR |
|---|---|---|---|
| Metastatic Cancers | | | |
| hMW | 81.0 (58.1, 94.6) | 87.8 (73.8, 95.9) | 3.4 |
| 92 kDa | 76.2 (52.8, 91.8) | 82.9 (67.9, 92.9) | 2.3 |
| 72 kDa | 28.6 (11.2, 52.2) | 100.0 (91.4, 100.0) | ND |
| hMW/ 72 kDa | 81.0 (58.1, 94.6) | 87.8 (73.8, 95.9) | 3.4 |
| Organ-Confined Cancers | | | |
| hMW | 53.2 (38.1, 67.9) | 87.8 (73.8, 95.9) | 5.0 |
| 92 kDa | 59.6 (44.3, 73.6) | 82.9 (67.9, 92.9) | 4.0 |
| 72 kDa | 34.0 (20.9, 49.3) | 100.0 (91.4, 100.0) | ND |
| 92/72 | 66.0 (50.7, 79.1) | 82.9 (67.9, 92.9 | 4.4 |
| All Cancers | | | |
| hMW | 61.8 (49.2, 73.3) | 87.8 (73.8, 95.9) | 8.4 |
| 92 kDa | 64.7 (52.2, 75.9) | 82.9 (67.9, 92.9) | 6.3 |
| 72 kDa | 67.6 (55.2, 78.5) | 100.0 (91.4, 100.0) | ND |
| 92/72 | 70.6 (58.3, 81.0) | 82.9 (67.9, 92.9) | 6.9 |

*These values are based on the ability of each MMP to discriminate between the Normal + NeD samples (n = 41) versus metastatic cancers (n = 21), organ confined cancers (n = 47) and all cancers (n = 68). CI = confidence interval; positive LR = positive likelihood ratio (ratio of true positives to false positives); ND = not defined because there were no false positives. hMW = high molecular weight MMP class migrating at greater than or equal to 150 kDa species. The results of the analysis of the combination of the 92 kDa and 72 kDa species, and of the hMW and the 72 kDa species are given when these markers were shown to be multivariate predictors in the logistic regression analyses.

Example 8

Disease Progression in Cancer Patients and Change in Enzyme Pattern

Patient Meta-4 (Table 4) was originally diagnosed with organ-confined CaP, and was subsequently diagnosed with metastasis, thus the data for this patient appear only in Table 4. Further, urine from patient Meta-6 which displayed 92 kDa MMP as shown, had been assayed 2 months prior to the data for that patient in Table 4, and was negative at that time for all MMP. These individual case histories show the diagnostic and prognostic value for cancer progression of the urine MMP pattern assay. These data showed that there was a high correlation (greater than 99%) of the presence of 72 kDa MMP in urine and presence of cancer.

Example 9

Additional Patient Data

A total of 68 cancer patient urine samples have been collected and analyzed for MMPs by the methods here.

TABLE 14

Gelatinase Profile.

| | Cancer Type | | | | | | Controls | |
|---|---|---|---|---|---|---|---|---|
| Metalloproteinases | Prostate | Renal | Bladder | Breast | Other | Metastatic | NeD | Normal |
| % with MMP | 75 | 40 | 80 | 100 | 64 | 90 | 11 | 23 |
| hMW | 57 | 30 | 70 | 100 | 64 | 86 | 5 | 18 |
| 92 kDa | 64 | 30 | 70 | 100 | 64 | 81 | 11 | 23 |
| 72 kDa | 39 | 30 | 30 | 10 | 36 | 29 | 0 | 0 |
| Creatinine (mg/dl): | 131 (±70*) | 134 (±78°) | 91 (±52) | 85 (±42) | 69 (±38) | 97 (±60) | 90 (±47) | 188 (±76) |

*±standard deviation;
hMW = high molecular weight
MMP class migration at greater than or equal to 150 kDa.

These include 28 patients with prostate cancer, 10 with renal cancer, 10 with bladder cancer, 9 with breast cancer, and 11 with other cancer (ovarian, lung, endometrial/cervical, testicular, lelomyosarcoma, adrenal pheochromocytoma, transitional cell carcinoma of kidney and lymphoma). These samples from patients with organ-confined cancers were compared to those from 19 patients with metastatic cancer, 19 former cancer patients with no evidence of disease, and 22 normal volunteers.

MMPs detected in the urine of patients with organ-confined disease and with metastatic cancer were compared to the normal/no evidence of disease control group. Sensitivity and specificity were calculated using standard formulas and expressed as percentages. The likelihood ratio was determined as the fraction of true positives divided by the fraction of false positives (sensitivity/100-specificity) to provide an indicator of the discriminating power for each MMP (Weinstein, M. C. Ed. Clinical Decision Analysis. Philadelphia: Saunders, pp. 84–108, 1980). Stepwise logistic regression was used to establish the independent predictors of cancer and to estimate the probability for combinations of the MMP markers in the final multivariate model. (Breslow, N. E. Statistical methods in cancer research. Volume 1. Lyon, France: Int. Agency for Res. on Cancer, pp. 192–210, 1980). One-way analysis of variance was performed to assess differences in creatinine levels among the groups with a Bonferroni correction for multiple comparisons. Fisher's exact test was used for comparison of proportions. All statistical tests were conducted at a two-sided alpha level of 0.05. Data analysis was performed using the SAS for Windows statistical package version 6.11 (SAS Institute Inc., Cary, N.C.).

Results shown in Tables 14 and 15 are consistent with previous data presented herein with smaller samples. Specificity of 72 kDa MMP for example, in prostatic cancer, all organ-confined cancer and all cancers is found to be 100 at the 95% confidence interval. For all cancers, the positive likelihood ratios (ratio of true positives to false positives) of the high molecular weight ≧150 kDA) and 92 kDa MMPs are 8.4 and 6.3, respectively. These results confirm the value of urine MMP zymogram routine analysis to detect the presence of cancer in particular, as an example of a tissue remodelling-associated condition, and for monitoring of cancer patients during therapy, and for prognosis of the course of cancer and the appearance of metastases.

Example 10
A Gelatinase Marker for Metastatic Breast Cancer

A gelatinase of approximately 125 kDa was detected in the urine of 5 out of 9 specimens obtained from metastatic breast cancer patients. Gelatinase of this size was not observed in urine samples of other subjects.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A non-invasive method for facilitating diagnosis of a subject for a cancer of epithelial origin, comprising:
   obtaining a urine sample from the subject; and
   detecting a presence or absence of a matrix metalloproteinase in the urine sample, wherein the matrix metalloproteinase has a molecular weight from 50 kDa to equal to or greater than approximately 150 kDa;
   wherein the presence of the matrix metalloproteinase is indicative of the presence of cancer of epithelial origin.

2. The method of claim 1, wherein the matrix metalloproteinase is a proenzyme.

3. The method of claim 1, further comprising removal of low molecular weight contaminants from the urine prior to the detection step.

4. The method of claim 1, wherein the urine is dialyzed.

5. The method of claim 1, wherein subject has previously been treated surgically or hormonally.

6. The method of claim 1, wherein the subject has been treated to block testosterone.

7. The method of claim 1, wherein the matrix metalloproteinase is a gelatinase.

8. The method of claim 1, wherein the matrix metalloproteinase has a molecular weight of approximately 72 kDa.

9. The method of claim 1, wherein the matrix metalloproteinase has a molecular weight of approximately 92 kDa.

10. The method of claim 1, wherein the matrix metalloproteinase has a molecular weight of approximately 150 kDa.

11. The method of claim 1, wherein the matrix metalloproteinase is detected or monitored electrophoretically.

12. The method of claim 11, wherein the electrophoretic pattern is a zymogram.

13. The method of claim 1, wherein the matrix metalloproteinase is detected or monitored immunochemically.

14. The method of claim 13, wherein matrix metalloproteinase is detected or monitored by a radio-immune assay.

15. The method of claim 13, wherein the matrix metalloproteinase is detected or monitored by an enzyme-linked immunosorbant assay.

16. A non-invasive method for facilitating diagnosis of a subject for a cancer of epithelial origin comprising:
   obtaining a urine sample from the subject; and
   detecting a presence or absence of at least two matrix metalloproteinases in the urine sample;
   wherein the presence of at least two metalloproteinases is indicative of the presence of cancer of epithelial origin.

17. A non-invasive method for facilitating diagnosis of a subject for a cancer of epithelial origin comprising:
   obtaining a urine sample from the subject; and
   detecting a presence or absence of an approximately 72 kDa and an approximately 92 kDa matrix metalloproteinase in the urine sample;
   wherein the presence of the approximately 72 kDa and the approximately 92 kDa matrix metalloproteinases is indicative of cancer of epithelial origin.

18. A non-invasive method for facilitating diagnosis of a subject for a cancer of epithelial origin comprising:
   obtaining a urine sample from the subject; and
   detecting presence or absence of an approximately 72 kDa in the urine sample;
   wherein the presence of the approximately 72 kDa matrix metalloproteinases is indicative of cancer of epithelial origin.

19. The method of claim 1, 16, 17, or 18, wherein the cancer of epithelial origin is selected from the group consisting of prostate cancer, cancer of the nervous system, breast cancer, retina cancer, lung cancer, skin cancer, kidney cancer, liver cancer, pancreatic cancer, cancer of the genital-urinary or gastrointestinal tract and bladder cancer.

20. The method of claim 16, 17, or 18, wherein the matrix metalloproteinase is a proenzyme.

21. The method of claim 16, 17, or 18, further comprising removal of low molecular weight contaminants from the urine prior to the detection step.

22. The method of claim 16, 17, or 18, wherein the urine is dialyzed.

23. The method of claim 16, 17, or 18, wherein subject has previously been treated surgically or hormonally.

24. The method of claim 16, 17, or 18, wherein the subject has been treated to block testosterone.

25. The method of claim 16, 17, or 18, wherein the matrix metalloproteinase is a gelatinase.

26. The method of claim 16, 17, or 18, wherein the matrix metalloproteinase is detected or monitored electrophoretically.

27. The method of claim 26, wherein the electrophoretic pattern is a zymogram.

28. The method of claim 16, 17, or 18, wherein the matrix metalloproteinase is detected or monitored immunochemically.

29. The method of claim 28, wherein matrix metalloproteinase is detected or monitored by a radio-immune assay.

30. The method of claim 28, wherein the matrix metalloproteinase is detected or monitored by an enzyme-linked immunosorbant assay.

31. The method of claim 16, wherein at least one of the matrix metalloproteinases has a molecular weight of approximately 72 kDa.

32. The method of claim 16, wherein at least one of the matrix metalloproteinases has a molecular weight of approximately 92 kDa.

33. The method of claim 16, wherein at least one of the matrix metalloproteinases has a molecular weight of equal to or greater than approximately 150 kDa.

* * * * *